United States Patent [19]

Shevitz

[11] 4,385,974
[45] May 31, 1983

[54] ELECTROPHORETIC SYSTEM AND METHOD FOR MULTIDIMENSIONAL ANALYSIS

[76] Inventor: Jerry Shevitz, 9 Alcott Dr., Livingston, N.J. 07039

[21] Appl. No.: 391,535

[22] Filed: Jun. 24, 1982

[51] Int. Cl.³ .................. B01D 57/02; G01N 27/26; G01N 27/30
[52] U.S. Cl. .......................... 204/180 G; 204/299 R; 436/516
[58] Field of Search ............... 204/180 G, 299 R; 436/516

[56] References Cited

U.S. PATENT DOCUMENTS

| | | | |
|---|---|---|---|
| 3,567,611 | 3/1971 | Michel et al. | 204/180 |
| 3,988,230 | 10/1976 | Krotz | 204/180 G |
| 4,061,561 | 12/1977 | Fletcher et al. | 204/299 R |
| 4,088,561 | 5/1978 | Anderson | 204/299 R |
| 4,101,401 | 7/1978 | Hoefer | 204/180 G |
| 4,305,799 | 12/1981 | Schwartz et al. | 204/180 G |

FOREIGN PATENT DOCUMENTS

| | | | |
|---|---|---|---|
| 2934479 | 3/1980 | Fed. Rep. of Germany | 204/180 G |
| 1150722 | 4/1969 | United Kingdom | 204/299 R |

Primary Examiner—Howard S. Williams
Assistant Examiner—T. F. Chapman
Attorney, Agent, or Firm—Natter & Natter

[57] ABSTRACT

A system for electrophoretic analysis includes four tanks, each of which carries an electrolytic solution which accesses a different edge surface of a pair of parallel gel plates. The gel plates include an electrophoretic separation path formed of a selected medium, e.g. an isoelectric focusing gel, extending in a space between the plates and across opposite edges of the plates. A pair of nonpolar barrier webs extend between the plates parallel to and on each side of the path. A different medium, e.g. a running gel, occupies the areas between the gel plates from the opposite sides of the barriers to the remaining edges of the plates. A pair of gaskets are positioned along plate edges which are perpendicular to the path. The gaskets include access apertures for the path and the barriers. A specimen is positioned within a channel leading from an electrolytic solution tank to the path aperture of a gasket and between a dam and the aperture. Electrophoretic separation of the specimen constituents within the separation path is achieved by current flow between a pair of tanks which communicate with the path through the gasket apertures. The barriers are removed preferably by aspiration after specimen separation. An equilibrating medium and gel are infused into the spaces previously occupied by the barriers and electrophoretic separation into the different medium is commenced by current flow between the remaining tanks which access the edges of the gel plates in communication with the different medium.

18 Claims, 7 Drawing Figures

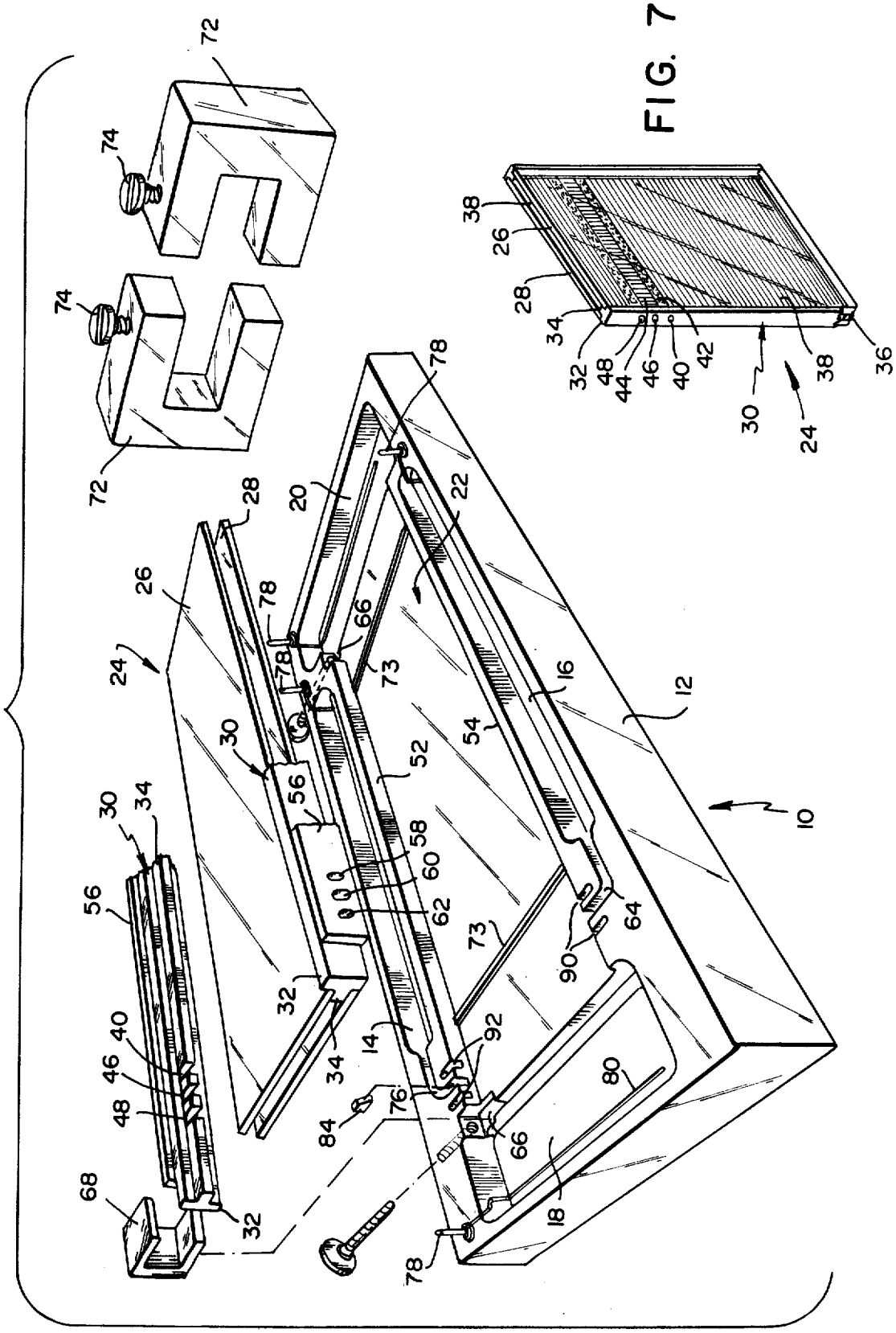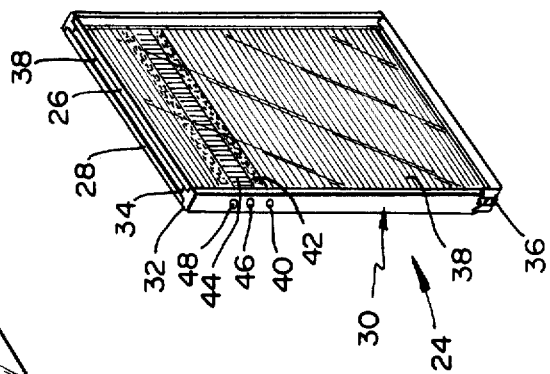

FIG. 4
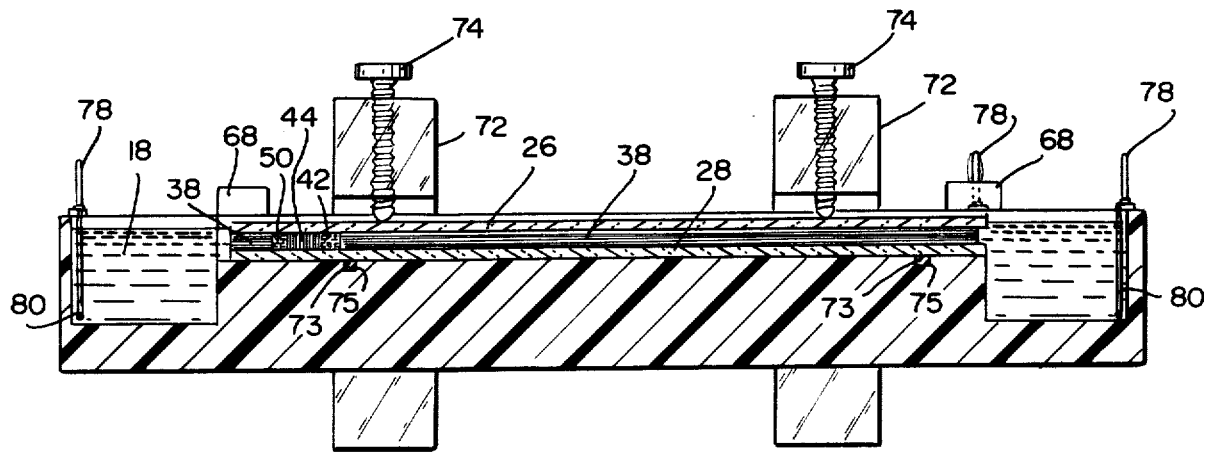
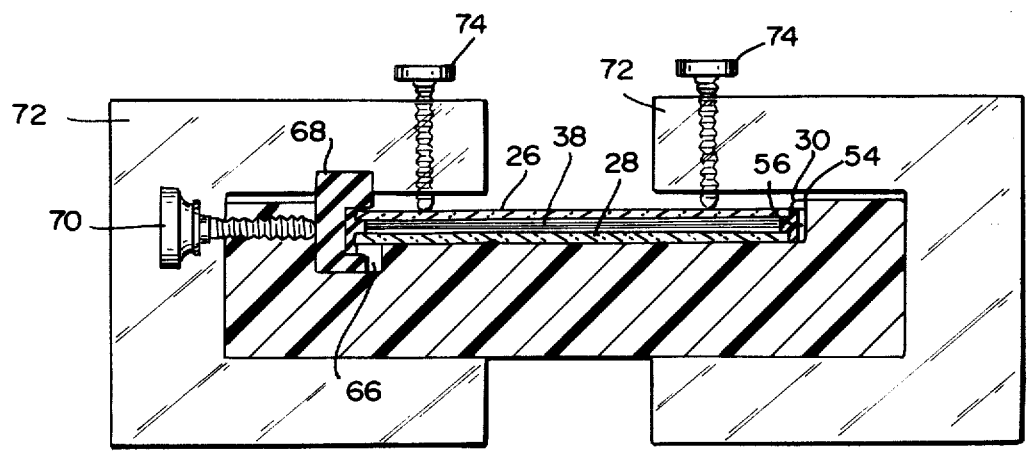
FIG. 5
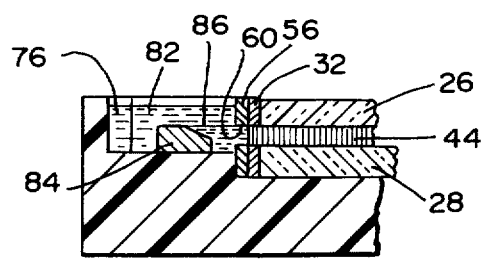
FIG. 6

4,385,974

ELECTROPHORETIC SYSTEM AND METHOD FOR MULTIDIMENSIONAL ANALYSIS

TECHNICAL FIELD

This invention relates generally to electrophoresis apparatus and more specifically to an apparatus and procedure for obtaining two dimensional electrophoretic separation.

BACKGROUND ART

When an electrical field was applied across a medium it caused charged particles to migrate within the medium as a function of the composition of the medium, the parameters of the electrical source and of the characteristics of the particles themselves. The composition of the medium and the parameters of the electrical source were reproducible factors so that the composition of particles which have migrated within the medium was accurately reflected in their relative positions after migration. Such phenomenon has been employed as the basis for electrophoresis.

Various electrophoretic systems have been used for separating complex mixtures of molecules. Both slab and columnar electrophoretic apparatus have been employed in conjunction with conducting media such as paper, agarose and polymers. A medium was positioned between two tanks which carried electrolytic solutions, and an electrical potential difference was applied across the tanks to produce migration of particles within the medium according to charge or size.

Identification of the different cell proteins by electrophoresis has become an analytic procedure of major significance in biological diagnostics.

Among the prior electrophoretic systems, separation of proteins according to differences in size has been achieved by employing a medium of sodium dodecyl sulfate polyacrylamide gel which has the potential to resolve $10^2$ different types of proteins out of the estimated $5 \times 10^4$ different proteins present in the human cell. A further electrophoretic analysis system comprised isoelectric focusing which separated proteins in a continuous pH gradient according to differences in isoelectric pH with a maximum resolution at $10^2$. Other methods and systems of electrophoresis yielded resolutions of similar magnitude.

It has been suggested that protein mixtures be separated according to both size and charge differences, and a combination of the two procedures has been termed two dimensional electrophoresis. The potential resolution of the two dimensional electrophoresis has been approximated at $5 \times 10^2$ with the coomassie blue staining method.

Various approaches have been attempted for optimized electrophoretic analysis through two dimensional electrophoresis. In one approach, a sample was first separated by isoelectric focusing within a rod shaped medium which, in turn, was carried in a glass tube. After completing the electrophoresis run, the medium was removed from the tube by mechanical means. Examples of removal techniques included mechanically applying pressure at one end of the tube to extrude the medium at the other end, injecting water between the medium and the tube, alternately freezing and thawing and even breaking the glass tube. In all of such attempts a high risk of damaging the medium was incurred.

The gel extraction procedure presented significant problems affecting reliability. A common supporting matrix in isoelectric focusing was 3% bis-acrylamide which forms a fragile gel. It was extremely difficult to maintain the original shape of the rod shaped medium. Pressure employed during removal, a syringe for injecting water between the rod and the tube or other extraction procedures often deformed or ruptured the rod medium.

After extraction, the separated rod medium was equilibrated to provide a uniform charge to the protein constituents and was placed horizontally on the upper portion of a vertical slab gel. The vertical slab gel was designed for protein separation according to size such as by sodium dodecyl sulfate polyacrylamide gel electrophoresis.

Approaches at two dimensional electrophoresis wherein a first run was achieved through a rod which thereafter was removed from a tube were typically illustrated in U.S. Pat. Nos. 4,305,799 and 4,088,561.

Although two dimensional electrophoresis possessed potential for superior diagnostic analysis due to high resolution capabilities, it has not been widely employed. Aside from the difficulty in rod medium removal which was a major disadvantage, the technique was subject to a relatively low degree of reproducibility. This was because isoelectric focusing electrophoresis apparatus and sodium dodecyl sulfate polyacrylamide gel electrophoresis apparatus varied in different laboratories based upon manufacturer and laboratory requirements.

A further problem encountered with prior two dimensional electrophoresis apparatus was that resolution was a function of media thickness. To optimize resolution, the rod media diameter must be minimized and the slab thickness minimized. In an isoelectric focusing run, high resolution could be obtained with a tubing diameter of 1 millimeter and a tubing length of 20 centimeters. While resolution was thus optimized, only a small amount of sample could be separated and only proteins of relatively high concentrations were detected.

It has been proposed to obtain two dimensional electrophoresis without removal of the medium after the first electrophoresis run. U.S. Pat. Nos. 4,101,401 and 4,061,561 are exemplary of such proposals to simplify two dimensional electrophoresis procedures. In U.S. Pat. No. 4,061,561 it was suggested that after an electrophoresis run through a slab medium, the slab be rotated 90 degrees and electrophoresis continue through the same medium in an orthogonal direction. This procedure only provided for a single type of separation.

In U.S. Pat. No. 4,101,401 two dimensional slab gel electrophoresis was suggested with a 90 degrees rotation of the slab. While different mediums were employed for each of the runs, high reliability of results have not been obtained due to a dispersion of the specimen constituents during the initial run. Applicant has determined that optimum results are obtained when the electric field is confined to a definite path such as that defined by a glass tube during the initial run. As a result, attempts at two dimensional electrophoresis as suggested have not provided satisfactory results.

DISCLOSURE OF THE INVENTION

A slab gel electrophoresis apparatus includes a separation path formed of a medium and extending between opposed parallel edges of a pair of gel plates. A nonconducting barrier web extends between the plates along each side of the separation path. The remaining space between the plates from the edges of each barrier web to the edges of the plates is occupied by a second medium.

The slab is horizontally positioned and clamped within a platen formed in the base of an electrophoresis apparatus. The base includes four electrolytic solution tanks with the solution of two tanks extending into channels formed in the base to opposed openings of slab edge gaskets in registry with opposite ends of the separation path. A specimen sample is positioned in one of the channels between the gasket opening and a dam formed in the channel. The elevation of the electrolytic solution is higher than that of the dam so that solution covers the specimen and the specimen is drawn into the separation path.

Access slots are provided in the base in registry with apertures in the gasket at the ends of each of the barrier webs. A suitable aspiration device such as a syringe is inserted into such apertures after a first run through the separation path and the barrier webs are aspirated.

Thereafter, a syringe is employed to equilibrate the specimen constituents in the separation path with a sodium dodecyl sulfate electrolytic buffer and an electrical potential is applied between a pair of electrolytic solution tanks which are in communication with the second medium along an electrical field orthogonal to the electrical field of the run through the separation path.

From the foregoing compendium, it will be appreciated that it is a feature of the present invention to provide an electrophoresis system and method for multidimensional analysis which is not subject to the disadvantages of the background art aforementioned.

A further feature of the present invention is to provide an electrophoresis system of the general character described with simplified operating procedures and enhanced diagnostic resolution.

A further aspect of the present invention is to provide an electrophoresis system of the general character described which permits two dimensional electrophoretic separation without moving the medium employed for electrophoretic separation in a first run.

A further aspect of the present invention is to provide an electrophoresis system of the general character described which is simple in operation yet provides reproducible results.

A still further feature of the present invention is to provide an electrophoresis method of the general character described for multidimensional analysis without the steps of manipulating specimen carrying mediums or supporting structures.

A further aspect of the present invention is to provide an electrophoresis system of the general character described wherein a specimen is overlaid with an electrolytic solution and confined for entry into a medium path.

A further feature of the present invention is to provide an electrophoresis system of the general character described for multidimensional analysis which is not limited in the media employable for isoelectric focusing.

Other aspects and features of the invention in part will be obvious and in part will be pointed out hereinafter.

With these features and aspects in mind, the invention finds embodiment in the various combinations of elements, arrangements of parts and series of steps by which the invention is achieved, all with reference to the accompanying drawings and the scope of which is more particularly pointed out and indicated in the appended claims.

BRIEF DESCRIPTION OF THE DRAWINGS

With reference to the accompanying drawings wherein one of the possible exemplary embodiments of the invention is illustrated;

FIG. 3 is an enlarged scale exploded perspective illustration of the electrophoretic apparatus with portions thereof broken away for clarity and showing the tanks;

FIG. 4 is a cross sectional view through the apparatus, the same being taken substantially along the plane 4—4 of FIG. 2 showing the gel slab structure and the clamping assembly;

FIG. 5 is a transverse cross sectional view through the apparatus, the same being taken substantially along the plane 5—5 of FIG. 2 and illustrating a self contained clamp for positioning the gel slab within the platen and compressing peripheral edge gaskets of the slab;

FIG. 6 is a fragmentary cross sectional view through the apparatus, the same being taken substantially along the line 6—6 of FIG. 5 and illustrating a dam structure in a solution channel which leads between a tank and a slab gasket aperture and depicting the manner in which a dense specimen is overlaid by the electrolytic solution for entry into a separation path; and FIG. 7 is a perspective illustration of a gel slab with portions of an edge gasket being broken away and illustrating the various media between the plates of the slab.

BEST MODE FOR CARRYING OUT THE INVENTION

Figure 1:
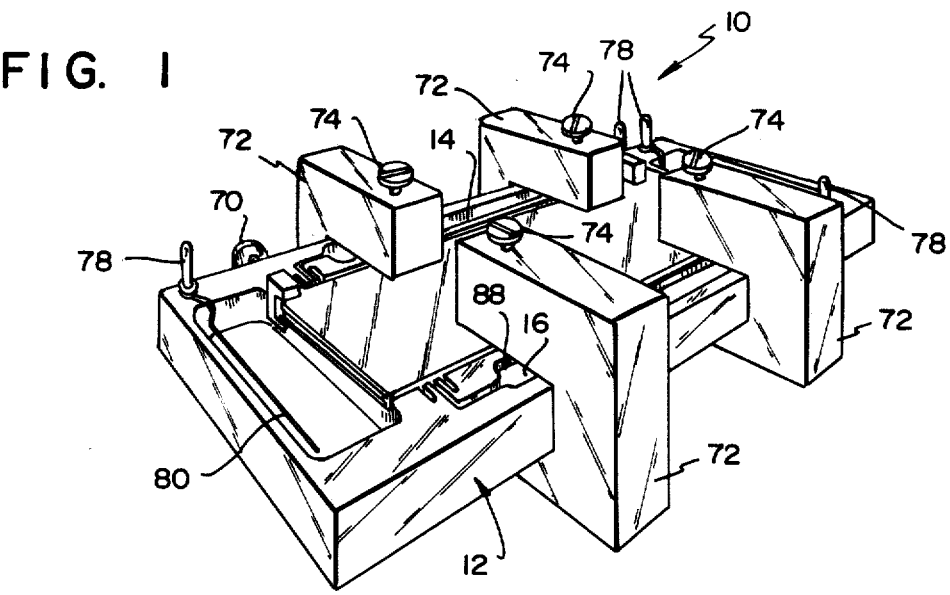
FIG. 1 is a perspective illustration of an electrophoresis system constructed in accordance with and embodying the invention and illustrating an electrophoresis apparatus having a base which includes four tanks, a platen for receiving a gel slab and a removable clamping assembly.

Referring now in detail to the drawings, the reference numeral 10 denotes generally an electrophoresis apparatus constructed in accordance with and embodying the invention. The apparatus 10 includes a monolithic base 12 which may be fabricated from a single block of acrylic or other suitable inert material.

A pair of elongate side tanks 14, 16 are formed adjacent the longitudinal edges of the base. Such tanks 14, 16 may be constructed, for example, by milling into the upper surface of the base. A pair of similarly formed end tanks 18, 20 are positioned adjacent opposite ends of the base. Between the tanks 14, 16, 18 and 20, a reduced height substantially rectangular platen 22 (FIG. 3) having a planar surface is provided. Conventional construction techniques other than milling, such as molding, may be employed to fabricate the entire base 12.

A gel slab 24 is releasably mounted in the platen 22. The gel slab is preformed of a pair of planar generally rectangular glass gel plates 26, 28 which extend parallel to one another. An elongated gasket 30 of T-shaped transverse cross section is positioned and adjacent the longitudinal edges of the gel plates 26, 28. As can be observed from FIGS. 3 and 7, the gasket 30 includes a generally planar web 32 for edge sealing of the gel plates and a spine 34 which projects perpendicular to the web intermediate its width. The spine 34 extends between the plates 26, 28 and serves as a spacer for maintaining a fixed distance between the gel plates. The gasket 30 is not necessarily compressible and at least the spine 34 thereof is substantially rigid. A suitable material for construction of the gasket 30 is polycarbonate; however thermoplastics such as polyethylene, polypropylene, ABS and polyamids may be employed. The spine is of a thickness selected to provide the desired degree of resolution.

To assemble the gel slab 24, the gel plates 26, 28 are positioned as illustrated in FIG. 7, and an elongated sealing spacer of square transverse cross section 36 is positioned along the bottom edges thereof to close the bottom space thereby permitting media to be inserted between the plates. The gel plate assembly is made leakproof by conventional methods.

With the gel plates vertically positioned as illustrated in FIG. 7 and with conventionally employed clamping devices maintaining the gel plates 26, 28, gaskets 30 and the bottom spacer 36 in position, a running gel medium is poured through the open upper end between the gel plates 26, 28.

The running medium is poured to an elevation slightly below that of a lower aperture 40 on each of the gaskets 30. It should be appreciated that the gaskets 30 on the left and right sides of the gel slab 24 are identical to each other. A thin layer of isobutanol may then be added over the upper surface of the running medium 38 for the purpose of avoiding evaporation and assuring uniform gelling.

Thereafter, a barrier web 42 of a nonconducting liquid such as glycerol is poured through the open top of the gel slab to a level just above the top of the gasket aperture 40. In order to temporarily seal the openings in the gasket 30, an elastic band may be stretched around the gel slab 24 covering all of such openings.

Following the glycerol barrier web 42, an isoelectric focusing gel medium 44 is then poured. The isoelectric focusing medium 44 is layered on top of the glycerol barrier web 42 from an elevation beneath that of a separation path aperture 46 to a level above such aperture 46 but beneath a higher elevation barrier web aperture 48.

After gelling of the isoelectric focusing medium 44, a further barrier web 50 of glycerol is poured to an elevation higher than that of the gasket aperture 48. The isoelectric focusing gel medium 44 is thus bordered by a pair of nonconducting barrier webs 42, 50 and is sandwiched in the space between the gel plates 26, 28 to provide a separation path for constituents of a specimen. The remaining space from the barrier web 50 to the top opening of the gel slab 24 is filled with additional running medium 38.

For the purpose of illustration only, the drawings indicate various colors for the running gel 38, the barrier webs 42, 50 and the isoelectric focusing gel 44. The color designations in the drawing have no relationship to the actual appearance of such media but merely serve to simplify the depiction of the invention.

The assembled gel slab 24 may be used immediately after the media gel or may be stored for subsequent use. Prior to use, the elastic band covering the gasket openings 40, 46, 48 and the bottom spacer 36 are removed.

Returning now to the base 12, the platen 22 includes a pair of side walls 52, 54 which are spaced apart a distance greater than the width of the gel slab and the gasket webs 32. The side walls 52, 54 extend upwardly perpendicular from the plane of the platen 22 to the upper surface of the base 12.

In accordance with the invention, the gel slab 24 is positioned on top of the platen and between the side walls 52, 54 thereof. In order to seal and position the slab gel, a pair of planar compressible gasket strips 56 are compressed between each gasket web 32 and its adjacent platen side wall. As illustrated in FIG. 3, the gasket strips 56 include suitable apertures 58, 60, 62, in registration with the apertures 40, 46, 48 respectively of the gasket 30.

When positioning the gel slab 24, a gasket strip 56 is first registered with the gasket 30 which is adjacent the platen wall 54. The central aperture 60 of the gasket strip 56 is generally placed in registration with the gasket opening 46 and an opening formed in the side wall 54 by a channel 64 which runs from the side tank 16 to the side wall 54.

Adjacent each of the ends of the side wall 52 a cutout 66 is formed in the base 12. The cutout 66 extends both downwardly from the elevation of the platen 22 toward the side wall of the base 12. Within each of the cutouts 66 a channel clamp 68 is positioned. From an examination of FIG. 5, it will be seen that such channel clamp 68 includes a pair of parallel legs between which the gel plates 26, 28 are received. Each of the channel clamps 68 is slidable within its cutout 66 toward or away from the side wall 54. A thumb screw 70 is received within a threaded bore of the base 12 in registry with the clamp 68 to force the bight of each clamp against the web 32 of the gasket 30 thereby urging the gel slab 24 toward the side wall 54 and causing the gasket strip 56 to compress.

With the gasket strip 56 compressed between the side wall 54 and the abutting gasket 30, a suitable space is provided between the opposite gasket 30 and the side wall 52. Within such space, a second gasket strip 56 is positioned so that its apertures are in registry with the associated opening of the gasket 30. The gasket strips 56 are shorter than the length of the gasket 30 so that the last positioned strip 56 can be slipped between the bights of the channel clamps 68. Once the gasket strip is positioned between the side wall 52 and the adjacent gasket 30, the clamp pressure is relieved by rotating the thumb screws 70. The gasket strip 56 which abuts the side wall 54 then expands which causes the gasket strip 56 abutting the wall 52 to compress. Thus both gasket strips 56 remain in a compressed state sealing the gel slab.

Two sets of "C" clamps 72 are slipped over the base 12 and a thumb screw 74 of each C clamp 72 is rotated to exert a downward force on the upper gel plate 26, thereby maintaining the gel slab 24 in a fixed position and forcing the gel plate 28 against the platen 22 and a pair of transverse sealing gaskets 73 which are seated in a pair of grooves 75 running across the platen 22 between the side walls 52, 54.

Figure 2:
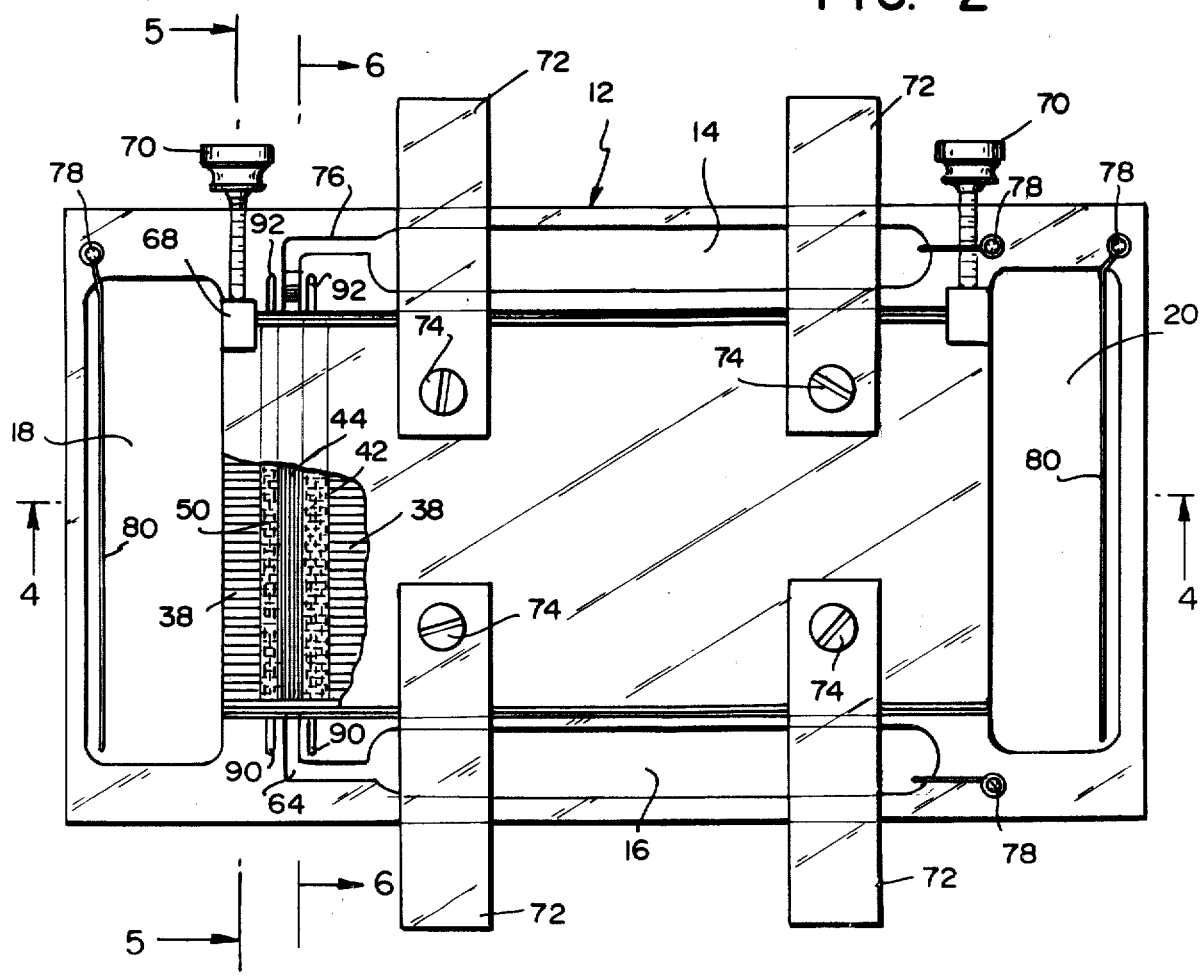
FIG. 2 is an enlarged scale top plan view of the apparatus with a portion thereof being broken away to better illustrate the construction of the gel slab.

As can be observed from FIGS. 2, 3 and 4, the end tanks 18, 20 are in contact with the opposite ends of the gel slab 24 and, as such, the transverse gaskets 73 prevent the flow of electrolytic solution directly between these tanks.

The channel 64 extends from the side tank 16 toward the end tank 18 and thence in a perpendicular direction into the side wall 54. Such channel is in registry with the gelled isoelectric focusing medium 44 of the separation path and accesses the separation path through the opening 46 in the gasket 30 and the aperture 60 in the gasket strip 56. The opposite side tank 14 is in communication with the separation path through a similar channel 76 which extends from the tank 14 to the side wall 52. The side tanks 14, 16 are filled with an electrolytic solution which accesses the separation path through the associated channel 64, 76 of each tank.

Associated with each of the tanks 14, 16, 18, 20 is a separate electrical terminal post 78 and a wire electrode 80 which extends from each terminal post into its respective tank. The electrode 80 extends along the length of the end tanks 18, 20.

Referring now to FIG. 6 wherein a portion of the channel 76 is illustrated, the electrolytic solution carried in the tank 14 and the channel 76 is denoted generally by the reference numeral 82. It will be observed that in the area of the channel 76 wherein the channel extends substantially perpendicular to the side wall 52, a dam 84 projects upwardly. The dam 84 includes a substantially perpendicular rear wall which extends to an elevation approximately equal to the elevation of the uppermost portion of the strip aperture 60. The dam 84 includes a downwardly sloped opposite wall which faces the aperture 60.

A specimen 86 is preferably positioned between the dam 84 and the separation path and confined to such area by the dam 84. The elevation of the electrolytic solution 82 is above that of the dam, however, the specimen is of a higher density than the electrolytic solution and remains between the dam and the separation path. To make the specimen dense, urea and/or glycerol may be mixed with the sample to concentrations of 1 molar or 10%.

An electrolytic solution 88 is carried in the tank 16 and specimen protein constituent separation by isoelectric focusing may be accomplished in the gelled separation path by applying an electrical potential across the terminal posts in engagement with the electrodes 80 of the tanks 14 and 16.

As previously mentioned, the barrier webs 42, 50 which border the sides of the isoelectric focusing medium 44 serve to confine the isoelectric focusing medium 44 to the definite separation path and constrict current flow and specimen separation to such path. The specimen 86 migrates into the separation path for separation of constituents in a continuous pH gradient on the basis of the isoelectric pH of such constituents. Pursuant to the invention, the current flow and the movement of specimen constituents is confined within the separation path defined by the barrier webs and the gel plates.

The barrier webs are preferably formed of a nonconducting liquid such as glycerol, an immiscible organic liquid or even air and are removed after the first run of isoelectric focusing has been completed. To prepare the apparatus 10 for an electrophoresis run in a second orthogonal direction in accordance with the invention, the barrier webs 42, 50 are removed.

As can be observed from FIGS. 1 and 2, a pair of grooves 90 are formed in the base 12 and extend into the side wall 54. The grooves 90 are positioned on each side of the channel 64 in the area of such channel which is perpendicular to the side wall 54. Similarly, a pair of grooves 92 are positioned in the base 12 adjacent the side wall 54 with one groove on each side of the channel 76.

The grooves 90, 92 are in registration with the gasket strip apertures 58, 62 and the gasket openings 40, 48 and are hence in communication with the barrier webs 42, 50. To remove the barrier webs 42, 50, the barrier liquid, e.g. glycerol, is aspirated through the use of a syringe positioned in each groove 90, 92. After the barrier webs are removed, an equilibration buffer is infused into the space previously occupied by the webs. A typical equilibration buffer may comprise 0.2 Tris buffer pH 6.5 and sodium dodecyl sulfate 5%. The equilibration buffer may include 3% bis-acrylamide as a gelling agent and bromphenol blue may be added as an indicator. A gel layer is required between the medium 44 and the medium 38 to restrict diffusion of particles during the migration of particles from the medium 44 to the medium 38. Such gel layer may be termed a stacking gel. The time required for gelling may be controlled by varying the amount of catalyst, e.g. TEMED and ammonium persulfate.

The sodium dodecyl sulfate of the equilibration buffer enters the medium 44 by diffusion and then combines with the constituent proteins separated in the separation path conferring a uniform negative charge in preparation for a second electrophoresis run. This procedure may be modified by first employing the equilibriating media without the gelling agent, aspirating such equilibrating media and then infusing additional equilibrating media with a gelling agent after the intial washing procedure. To reduce the time required to equilibrate the particles in the medium 44, the equilibration buffer constituents may be caused to migrate into the separation path by applying a short duration electrical potential across the end tanks 18, 20, each of which carries an electrolytic solution.

Thereafter, the second electrophoresis run may be commenced by applying a suitable electrical potential between the tanks 18, 20. The degree of such migration of particles from the separation path into the running gel is also indicated by the bromphenol blue indicator.

The sodium dodecyl sulfate infused into the area previously occupied by the barrier web 50 migrates towards the tank 20, whose electrode 80 is an anode, into the gelled isoelectric focusing medium 44 prior to significant movement of the proteins out of the isoelectric focusing medium and into the gelled equilibrating medium which occupies the space of the aspirated barrier web 42. This is in part due to the high charge to size ratio of the buffer and the sodium dodecyl sulfate as compared to the peptides in the medium 44. The movement of sodium dodecyl sulfate into the medium 44 may be monitored by the movement of the indicator bromphenol blue in the same equilibriating medium. It should also be noted that the barrier web 42 intermediate the separation path and the gelled medium 38 may be wider than the barrier web 50. The increased width provides for improved stacking of particle migration from the medium 44 to the medium 38, thus improving resolution of the separation.

During the second electrophoresis run, specimen separation is continued in an orthogonal plane according to particle size rather than isoelectric pH. Particle separation extends into the gelled running medium 38 between the gelled equilibration buffer and the end tank 20. In addition, particle separation may be obtained in the gelled running medium 38 between the opposite equilibration buffer and the end tank 18 with omission of sodium dodecyl sulfate from the equilibration buffer.

After completion of the second run, the positions of the separated particles in the running gel are observed through conventional techniques.

It should be appreciated that because isoelectric focusing gel manipulation is not required prior to commencing the electrophoresis run in the running gel, the invention is not limited in the types of media which can be employed. For example, agarose may be substituted for bis-acrylamide as a supporting matrix for isoelectric focusing.

The greater permeability of agarose permits separation of molecules of large molecular weight which is not possible when bis-acrylamide gel is used. In addition, the permeability of agarose facilitates a rapid separation of particles and rapid equilibration with sodium dodecyl sulfate prior to the orthogonal direction run.

As employed herein, the isoelectric focusing medium 44 and the running medium 38 may comprise any of a number of conventional formulations well known to those of skill in the art and described in numerous publications.

By way of example, a typical running medium may comprise: bis-acrylamide 10%, a Tris buffer, 0.4 M, pH 8.8 sodium dodecyl sulfate, 0.1% and catalysts such as TEMED and ammonium persulfate.

A typical isoelectric focusing medium may comprise: Ampholines for establishing a pH gradient, urea and gelling agents such as bis-acrylamide or agarose.

In addition, the electrolytic solutions employed in the various tanks may comprise any of a number of conventional formulations.

Typical publications wherein suitable medium and buffer formulations are disclosed include: Tuszynski, et al.—

*A Two-Dimensional Polyacrylamide Gel Electrophoresis (PAGE) System Using Sodium Dodecyl Sulfate-PAGE in the First Dimension,* Analytical Biochemistry 93, pp. 329–338 (1979), Weber, et al.—*Proteins and Sodium Dodecyl Sulfate: Molecular Weight Determination on Polyacrylamide Gels and Related Procedures,* Journal of Biological Chemistry, Vol. 244, pp. 4406–4412 (1970), and Epstein, et al.—*Peptide Mapping of Contractile Proteins: Two-Dimensional Analysis of cyanogen Bromide Fragments on Polyacrylamide Gels,* Analytical Biochemistry 76, pp. 157–169 (1976), all of which are incorporated herein by reference.

It should be noted that the barrier web 50 need not always be replaced with a gelling medium. A liquid medium may be employed when further modification of particles is desired during the run in the second dimension. This technique may be employed by infusing sodium dodecyl sulfate or agents which selectively react with specific particles, for example antibody-antigen reactions without sodium dodecyl sulfate.

As various changes might be made in the invention as above set forth, it is to be understood that all matter herein described or shown in the accompanying drawings is to be interpreted as illustrative and not in a limiting sense.

Thus, it will be seen that there is provided an electrophoresis system which includes the various features and aspects of the invention and which is well suited to meet the conditions of practical use.

Having thus described the invention, there is claimed as new and desired to be secured by Letters Patent:

1. An apparatus for conducting electrophoretic analysis, the apparatus comprising means for supporting an electrophoresis gel slab, the gel slab including a separation path comprising a first gel and defined by the space between a pair of parallel gel plates and a pair of barrier webs, the gel slab further including a second gel positioned in the space between the gel plates and adjacent at least one barrier web, the apparatus further comprising means forming a first pair of tanks for carrying an electrolytic solution and electrode means communicating with the electrolytic solution in each tank, means accessing the solution of each tank to opposite ends of the separation path, means for accessing the barrier webs for aspiration of the barrier webs from the gel slab after electrophoretic separation of a specimen in the separation path, the accessing means including means for permitting the infusion of an equilibrating medium into the spaces between the gel plates previously occupied by the barrier webs, the apparatus further including a second pair of tanks for carrying an electrolytic solution and electrode means communicating with the solution in each of the tanks of the second pair, means for accessing the solution of each tank of the second pair with the second gel, the specimen particles separated in the separation path being further separated by particle size in the second gel when an electrical potential is applied between the solutions in each of the tanks of the second pair, whereby two dimensional electrophoretic analysis is obtained without the necessity of manipulating the gel of the separation path.

2. An apparatus for conducting electrophoretic analysis constructed in accordance with claim 1 wherein the means for supporting the gel slab includes a generally flat planar platen and a pair of parallel side walls, the means for accessing the barrier webs including means forming slots in the side wall in registry with the barrier webs whereby a syringe may be placed within the slots for aspirating the barrier webs.

3. An apparatus for conducting electrophoretic analysis constructed in accordance with claim 1 further including a monolithic base, the tanks being formed as depressions in the base and the means for supporting the gel slab comprising a platen formed in the base.

4. An apparatus for conducting electrophoretic analysis constructed in accordance with claim 1 wherein the means for supporting the electrophoresis gel slab comprises means forming a generally planar platen, the platen including a pair of parallel upstanding side walls, the apparatus further including a pair of elongate compressible gaskets, and means for compressing each gasket between the gel plates and one of the side walls of the platen, the compressing means comprising clamping means positioned adjacent one of the side walls for urging the gel plates toward the other side wall to compress one compressible gasket between the gel plates and the other side wall thereby providing an enlarged space between the gel plates and the one side wall, the space being of a width greater than the thickness of a compressible gasket, the other compressible gasket being positioned in such space and the compressing means being thereafter released.

5. An apparatus for conducting electrophoresis analysis constructed in accordance with claim 1 wherein the means accessing the solution of the first pair of tanks to opposite ends of the separation path includes means forming a channel between one of the first tanks and one end of the separation path, the apparatus further including means for introducing a specimen into the separation path, the specimen introducing means comprising means forming a dam in the channel, the dam extending to an elevation beneath the elevation of a solution in the channel, the dam being positioned adjacent one end of the separation path, the specimen being positioned between the one end of the separation path and the dam, the solution extending to an elevation above that of the specimen.

6. An apparatus for conducting electrophoretic analysis constructed in accordance with claim 5 wherein the dam extends to an elevation at least as high as the elevation of the separation path.

7. An apparatus for conducting electrophoretic analysis constructed in accordance with claim 5 wherein the specimen includes means for increasing its density.

8. An electrophoresis gel slab suitable for two dimensional electrophoretic analysis, the gel slab comprising a pair of substantially rectangular gel plates having parallel side edges and ends, means maintaining the gel plates uniformly spaced from one another in parallel planes, one gel positioned between the plates, and one gel extending substantially across the side edges of the plates from one end of the plates to a distance less than the distance between the end surfaces of the plates, a first barrier web of nonconducting material positioned between the plates, the first barrier web extending substantially across the side edges in juxtaposed relationship to the one gel, the further gel extending substantially across the side edges of the plates in juxtaposed relationship to the first barrier web, a second barrier web positioned between the plates, the second barrier web extending substantially across the side edges of the plates in juxtaposed relationship to the further gel.

9. An electrophoresis gel slab constructed in accordance with claim 8 further including an elongate gasket positioned adjacent each of the side edges, and means forming an opening in each of the gaskets in registration with the ends of the further gel.

10. An electrophoresis gel slab constructed in accordance with claim 9 further including means forming an opening in the gaskets adjacent each of the ends of the barrier webs.

11. An electrophoresis gel slab constructed in accordance with claim 10 wherein the means maintaining the gel plates uniformly spaced from one another comprises a spine projecting between the plates from each of the gaskets.

12. An electrophoresis gel slab constructed in accordance with claim 8 further including a third gel, the third gel being positioned in the space between the plates in juxtaposed relationship to the second barrier web and extending substantially across the side edges of the plates to the remaining end of the gel plates.

13. An electrophoresis gel slab constructed in accordance with claim 8 further including a layer of isobutanol intermediate the one gel and the first barrier web.

14. An electrophoresis gel slab constructed in accordance with claim 8 wherein the further gel comprises an isoelectric focusing gel and includes a bis-acrylamide supporting matrix.

15. An electrophoresis gel slab constructed in accordance with claim 8 wherein the further gel includes an agarose supporting matrix.

16. A method of obtaining a two dimensional electrophoretic analysis of a specimen with a gel slab constructed in accordance with claim 8 comprising the steps of:
   (a) accessing the opposite ends of the further gel with separate electrolytic solution;
   (b) accessing the further gel with a specimen;
   (c) causing the specimen to separate in the further gel by applying an electrical potential across the separate electrolytic solutions;
   (d) removing the barrier webs from the gel slab by aspiration;
   (e) infusing an equilibrating medium in the spaces occupied by the barrier webs;
   (f) forming a stacking gel in the spaces occupied in the barrier webs;
   (g) accessing the one gel with a buffer solution; and
   (h) causing the previously separated specimen to migrate into the one gel by applying an electrical potential between the one gel electrolytic solution and the further gel.

17. A method of obtaining an electrophoretic analysis of a specimen as set forth in claim 16 wherein the gel slab further includes a third gel positioned between the gel plates in juxtaposed relationship to the second barrier web, the method further including the step of accessing the third gel with an electrolytic solution, the electrical potential at the further gel being applied by applying an electrical potential across both the one gel electrolytic solution and the third gel electrolytic solution.

18. A method of obtaining a two dimensional electrophoretic analysis of a specimen in accordance with claim 16 wherein the barrier webs are aspirated with a syringe and the equilibrating medium is infused with a syringe.

* * * * *